| United States Patent [19] | [11] | 4,002,576 |
|---|---|---|
| Gregory et al. | [45] | Jan. 11, 1977 |

[54] ENZYME CARRIER REGENERATION

[75] Inventors: Jerry L. Gregory; Wayne H. Pitcher, Jr., both of Painted Post, N.Y.

[73] Assignee: Corning Glass Works, Corning, N.Y.

[22] Filed: July 18, 1975

[21] Appl. No.: 597,012

[52] U.S. Cl. .............................. 252/415; 252/412;
195/31 F; 195/63; 195/68; 134/39
[51] Int. Cl.² .................. B01D 15/06; C12B 1/00;
C12K 1/00
[58] Field of Search .......... 252/412, 415; 195/31 F,
195/63, DIG. 11; 134/2, 39

[56] References Cited

UNITED STATES PATENTS

| 3,671,179 | 6/1972 | Jinnette | 134/2 X |
| 3,894,884 | 7/1975 | Druin et al. | 134/25 R |

Primary Examiner—Patrick P. Garvin
Assistant Examiner—William G. Wright
Attorney, Agent, or Firm—James A. Giblin; Clinton S. Janes, Jr.; Clarence R. Patty, Jr.

[57] ABSTRACT

Highly porous $MgO-Al_2O_3$ particulate support materials useful for the immobilization of glucose isomerase can be regenerated for reuse by circulating a sodium hypochlorite solution through the particles thereby permitting in situ enzyme carrier regeneration.

6 Claims, No Drawings

ENZYME CARRIER REGENERATION

RELATED APPLICATIONS

Patent application Ser. No. 507,209 filed in the names of D. L. Eaton et al. entitled "Immobilized Glucose Isomerase" and patent application Ser. No. 507,199 now U.S. Pat. No. 3,965,035 filed in the names of L. R. Bialousz et al., both applications filed on Sept. 18, 1974 and assigned to the present assignee.

BACKGROUND OF THE INVENTION

1. Field

This disclosure is concerned generally with porous inorganic support materials useful for the immobilization of enzymes. Specifically, this disclosure is concerned with an improved method of regenerating certain porous inorganic support materials which have been used for the immobilization of glucose isomerase.

2. Prior Art

In U.s. Pat. No. 3,868,304, there are disclosed methods of immobilizing glucose isomerase within the pores of highly porous alumina particles to provide a very efficient and reuseable immobilized glucose isomerase system useful for the enzymatic isomerization of glucose (dextrose) to fructose (levulose). As described in that patent, it had been found that the porous alumina carrier for the enzyme should be in particulate form (e.g. within 4–200 mesh) and have an average pore diameter within the range of about 100A to 1000A, preferably within the range of about 180A to about 220A. In patent application Ser. No. 507,209, cited as a related application, an improvement over the alumina carrier is disclosed. The improved glucose isomerase carriers have incorporated thereinto varying amounts of magnesia, the preferred carriers consisting of both alumina and magnesia with the magnesia constituting about 0.84 to 12.0% by weight. Such carriers are referred to herein as $MgO-Al_2O_3$ carriers to distinguish them from the $Al_2O_3$ carriers.

In using particles of either porous $Al_2O_3$ or porous $MgO-Al_2O_3$ for the adsorption and, hence, immobilization of glucose isomerase, it has been found that the resulting composites demonstrate a high degree of stability and relatively long enzymatic half-lives. These qualities make the composites commercially attractive since such characteristics are desirable for any large scale conversion of glucose-containing solutions to sweeter fructose-containing solutions. The desirability of being able to continuously and economically convert glucose to fructose is well recognized, especially via enzymatic isomerization methods.

Even though the above-described porous $Al_2O_3$ and porous $MgO-Al_2O_3$ carriers can be used to prepare immobilized glucose isomerase composites having relatively long half-lives, the use, espeically the continuous use, of such composites is economically time-limited. Regardless of the length of enzymatic half-life of the composites, it can be appreciated that the total enzymatic activity tends to decline with time. Thus, at a given point in time, it becomes uneconomical to continue using the composites because of reduced activity. Accordingly, at that time it becomes more economical to simply replace the spent composite with fresh composite.

Although the above-described porous carriers are relatively inexpensive and may be discarded after use without detracting significantly from the overall favorable economics of using such carriers for glucose isomerase, the reuse of those carriers is highly desirable. Carrier reuse permits yet further economies and also avoids problems associated with discharge of the spent composite. It is known that various pyrolysis treatments can be used to burn off organic constituents on inorganic materials. However, as pointed out in patent application Ser. No. 507,199 cited above, simply pyrolysis does not assure the removal of all contaminants (e.g. various metal ions from the substrate) which tend to minimize subsequent enzyme reloading and half life. In the above patent application, a two step method of regenerating such carrier is disclosed. In the first step, the spent enzyme composite is pyrolyzed at a temperature ranging from about 500° to 900° C under conditions sufficient to remove essentially all carbonaceous material. Then the carrier is reacted with a neutralized citrate solution to assure removal of remaining contaminants. Although the cited two step method is effective in permitting regeneration of the $MgO-Al_2O_3$ carriers, it can be appreciated that the pyrolysis step generally requires removal of the spent composite from its container (e.g. a flow through column) and placement in an appropriate furnace. This is followed by removal from the furnace, replacement in the column and treatment with the citrate solution.

We have now found that the above regeneration steps can be replaced with a relatively simple one step regeneration technique which does not require pyrolysis. The regeneration step can be accomplished by fluidizing the spent composite in its original in-use container thereby obviating spent composite removal. Details of our method are described hereunder.

SUMMARY OF THE INVENTION

Our method of regenerating the highly porous and particulate $MgO-Al_2O_3$ carrier materials useful for the immobilization of glucose isomerase comprises the steps of circulating a sodium hypochlorite solution through the carrier particles under conditions sufficient to assure the removal of substantially all carbonaceous material and contaminants. In preferred embodiments, the sodium hypochlorite solution consists of at least about 5% by weight sodium hypochlorite in water and the regeneration is carried out in a fluidized bed containing the spent composite. Very preferably, the amount of solution used is at least about 5 ml per gram of spent composite and that solution is circulated through a bed of the composite particles for at least about 15 minutes.

SPECIFIC EMBODIMENTS

As pointed out above, the present invention is directed specifically toward an improved method of regenerating the porous, particulate $MgO-Al_2O_3$ carriers described in greater detail in Ser. No. 507,209. In general, those carriers comprise porous $MgO-Al_2O_3$ materials consisting of alumina and about 0.84% to about 12.0% magnesia (by wt.). For reasons given in the copending applications, it has been found that the average particle size of the porous carriers should be within the range of about 4 to 200 mesh, U.S. Standard Sieve, preferably about 30 45 mesh. The average pore diameter is within the range of about 100 to 1000A, preferably within the range of about 100 to 500A to assure as large a surface area as possible and to be consistent with molecular entry and diffusional limitations. Very specifically, it had been found that an ideal carrier for the immobilization (by adsorption) of glucose isomerase has an average pore diameter between about 150 and 250A. More recently, it has been found the average pore diameter can be up to about 400A. Since the MgO-Al$_2$O$_3$ carrier of patent application Ser. No. 507,209, is an especially preferred carrier for the preparation of an immobilized glucose isomerase composite, our present regeneration method is directed specifically toward that carrier although it is thought the regeneration step would also work well on the substantially pure alumina carriers disclosed in U.S. Pat. No. 3,868,304.

Our improved regeneration method is carried out in a fluidized bed by recirculating the sodium hypochlorite solution through the "spent" enzyme composite of patent application Ser. No. 507,209. As used herein, the expression spent composite, or its equivalent refers to the immobilized glucose isomerase composite using a MgO-Al$_2$O$_3$ carrier which, after some use, has become uneconomical to use further. Several factors may determine the point in time at which the composite is uneconomical to use. For example, the enzymatic half life or amount of active glucose isomerase on the carrier may have dropped to a relatively low level. The composite may have become contaminated with various microbial growths which preclude further economical use. Further, the composite may be contaminated with an undesirable excess of various metal ions which become associated with the composite after prolonged contact with the glucose containing solution, to which various buffers containing such ions are often added. As shown in Ser. No. 507,209, a preferred reactor system for the continuous conversion (isomerization) of glucose of fructose consists of a plugged flow-through column through which a buffered solution is continuously passed. The glucose solution is commonly buffered to a pH range in which optimum isomerization can occur and the temperature of the glucose solution and/or the column is commonly elevated, also to assure optimum isomerization without significant enzyme deactivation.

In using such a continuous processing system, various ions from the buffers tend to associate with the composite, the amounts of which tend to increase with time. As pointed out in Ser. No. 507,199 a relatively simple pyrolysis step does not assure the removal of such ions from a spent carrier. Rather, simple pyrolysis tends to leave residual metal oxide contaminants in and on the carrier surface. Since the accumulation of such metals tends to minimize the economical reuse of the spent carrier, it is highly desirable to have them removed to bring the porous carriers back to a near pristine condition prior to the adsorption of the active glucose isomerase. This need to remove such metal contaminants lead to the discovery that if a simple pyrolysis step is followed by a neutralized citrate wash, the spent carriers could be effectively regenerated for use.

The present method is an improvement over the above method in two major respects. Firstly, a pyrolysis step is not needed. Secondly, it is not even necessary to remove the spent carrier from its flow through column. We have found that the spent carrier can be fluidized in the column by circulating the sodium hypochlorite through the column exit under controlled conditions until the carrier is regenerated for reuse.

In the examples below, the MgO-Al$_2$O$_3$ carrier consisted of 30 to 45 mesh porous particles having an average pore diameter ranging from about 190 to 210A and consisting of about 2.2% by weight MgO. A one time "use" of the immobilized glucose isomerase using such carriers consisted of placing in columns about 15 g quantities of the composite consisting of the glucose isomerase adsorbed to the MgO-Al$_2$O$_3$ particles in accordance with the directions of Ser. No. 507,209 and then continuously passing a glucose-containing solution through the column at a flow rate of about 3 to 4 ml per min. The glucose solutions contained 0.005 M MgCl$_2$ and was buffered to a pH of about 8.4. Each column was deemed spent after having been used for an enzymatic half life of the composite (about 30 days). Glucose isomerase activity was measured in International Glucose Isomerase Units (IGIU) in accordance with the method described more fully in Ser. No. 507,199.

EXAMPLES

In the experiments below, spent enzyme composites were regenerated by circulating varying amounts and concentrations of an aqueous NaOCl solution through the columns containing the spent immobilized enzyme. The amounts of composite in each column ranged from about 15 g at start down to about 4 g with the successive regenerations. In the regeneration steps, the goal is to provide a reusable carrier capable of as high an enzyme re-loading as possible. To be economically feasible, we have found that glucose isomerase composites should demonstrate an in use loading of about 600 IGIU per gram of composite. Hence, any regeneration of carrier which could assure such loading can be deemed successful.

It was found that to a limited extent, the amount of NaOCl solution used in the regeneration had some effect on subsequent enzyme reloading. Preferably, at least about 5 ml of a 5% NaOCl solution is used per gram of carrier to be regenerated. As the amount of NaOCl solution was increased, it was found that there occured an increase in enzyme reloading. For example, in one set of experiments about 1800 IGIU of enzyme was offered per gram of carrier for adsorption. After use in column (30 days) this material (15 g total) was treated in a fluidized bed reaction with 5 mg/g of NaOCl solution for 15 min. at a flow rate of about 60 ml per min. This carrier was then offered about 2700 IGIU/g which resulted in an observed (in-column) activity of 800 IGIU/g as opposed to 700 IGIU/g for new carrier offered the same amount/g of enzyme. After operational use, the carrier was treated with 5 ml/g of 5% NaOCl solution and offered 2700 IGIU/g enzyme resulting in only 542 IGIU/g activity. However, after a subsequent treatment with 13.3 ml/g of 5% NaOCl, the activity following identical enzyme immobilization was 864 IGIU/g.

The following table shows the relatively high level of loading activity observed after spent composite had been regenerated with varying amounts of a 5% NaOCl solution. The original (unregenerated) carrier was initially offered 3500 IGIU/g of enzyme. After the regeneration step, the carriers were offered 2700 IGIU/g of enzyme. The regeneration step was accomplished by recirculating the indicated NaOCl solutions through approximately 15 g quantities of spent composite for about 120 minutes.

Table I

| Treatment (ml 5% NaOCl per gram carrier) | Initial Activity using regenerated carrier (IGIU/g) |
|---|---|
| 5 | 651 |
| 10 | 709 |
| 13.3 | 809 |

After the above treatments, the carriers were rinsed in distilled water prior to adsorption of the enzyme. However, in a subsequent experiment, it was found that if enzymes were absorbed to the carrier (no water rinse) after a 15 minute treatment with 5 ml/g of 5% NaOCl, the resulting activity of the composite having the regenerated carrier was 824 IGIU/gram.

TABLE II

Increasing the NaOCl treatment time did not increase effective enzyme loading

| time (min.) | NaOCl (%) | Amt. (ml sol'n/g) | Initial Activity (IGIU/g) |
|---|---|---|---|
| 120 | 5 | 5 | 799 |
| 15 | 5 | 5 | 810 |
| 15 | 5 | 5 | 797 |

No advantage was found in additional increase of the amount NaOCl used:

| | | | |
|---|---|---|---|
| 30 | 5 | 10 | 773 |
| 60 | 5 | 20 | 716 |

Varying the concentration and source (using commercial bleach*) of NaOCl did not affect results.

| | | | |
|---|---|---|---|
| 15 | 2.5 | 10 | 774 |
| 15 | 5.75 | 5 | 807* |

MULTIPLE REGENERATIONS

Using a substantially similar MgO-Al$_2$O$_3$ carrier preparation (but from a different lot No.) the spent carriers were regenerated several times over as indicated below. As shown below, the same carrier preparation (about 15 g of 2.2% MgO, 97.8% Al$_2$O$_3$, 30 to 45 mesh, 190A avg. pore diameter) was regenerated four times with no observable loss in enzyme loading capability. In fact, a slight increase was noted.

As indicated, on the fifth regeneration attempt, the highest loading obtained after three attempts was 521 IGIU/g. At that point, the carrier was subjected to a pyrolysis treatment (600° C for 3 hours). Then, six more acceptable regenerations were performed using the NaOCl treatment. In all multiple regeneration experiments about 10 to 20 ml/g of 5% NaOCl was used for 15 min. at 250° C in the "fluidized bed reactor" column. Approximately 15 g samples were regenerated initially with some carrier loss on subsequent regenerations.

TABLE III

| Regeneration Number | Initial Activity IGIU/g | Half-life (days) 95% confidence | | |
|---|---|---|---|---|
| | | mean | LCL | UCL |
| 0 | 700 | 30 (Avg. value) | | |
| 1 | 793 | 23.5 | 22.0 | 25.1 |
| 2 | 905 | 27.9 | 26.1 | 29.9 |
| 3 | 789 | 41.3 | 37.6 | 46.0 |
| 4 | 713 | 31.7 | 24.7 | 44.2 |
| 5 | 521* | | | |

*The maximum value of 521 IGIU/g was achieved after three regeneration attempts. Then the sample was pyrolyzed and regenerated 6 more times with the NaOCl solution as indicated.

| | 874 | 34.9 | 32.7 | 37.3 |
|---|---|---|---|---|
| 6 | 835 | 29.9 | 28.0 | 32.0 |
| 7 | 796 | 27.4 | 24.4 | 31.3 |
| 8 | 673 | 36.5 | 32.4 | 41.6 |
| 9 | 787 | 33.8 | 30.7 | 37.6 |
| 10 | 600 | 21.6 | 19.0 | 25.1 |
| 11 | 706 | 19.5 | 16.5 | 23.8 |

We claim:
1. A method of regenerating a spent immobilized glucose isomerase composite comprising glucose isomerase adsorbed to porous particles of a MgO-Al$_2$O$_3$ carrier and having associated therewith carbonaceous material and contaminants resulting from use of the composite for the continuous isomerization of glucose to fructose, the method comprising the step of fluidizing the spent composite particles in a fluidized bed reactor by circulating a sodium hypochlorite solution through the composite under conditions sufficient to remove substantially all carbonaceous material and contaminants.
2. The method of claim 1 wherein the amount of NaOCl solution consists of an aqueous solution of at least about 5% by weight NaOCl, the amount of solution being about 5 ml per gram of support material to be regenerated.
3. The method of claim 1 wherein the regeneration step is for at least about 15 minutes.
4. The method of claim 1 wherein the regeneration step comprises circulating at least a 5% by weight aqueous NaOCl solution through the carrier particles contained in a fluidized bed reactor for at least about 15 minutes, the amount of solution being about 5 ml per gram of carrier.
5. The method of claim 1 wherein the support material comprises porous particles of a MgO-Al$_2$O$_3$ composition, the amount of MgO ranging from about 0.84 to 12.0% by weight, the particles having an average pore diameter ranging from about 100 to 1000A and an average particle size ranging from about 4 to 200 mesh, U.S. Standard Sieve.
6. The method of claim 1 wherein the average pore size ranges from about 100 to 250A.

* * * * *

UNITED STATES PATENT AND TRADEMARK OFFICE
CERTIFICATE OF CORRECTION

PATENT NO. : 4,002,576

DATED : January 11, 1977

INVENTOR(S) : Jerry L. Gregory and Wayne H. Pitcher, Jr.

It is certified that error appears in the above-identified patent and that said Letters Patent are hereby corrected as shown below:

Column 2, line 8, "507,199cited" should be -- 507,199, cited --.

Column 2, line 63, "30 45" should be -- 30 to 45 --.

Column 3, line 17, "spent" (without quotes), should be -- "spent" --.

Column 3, line 34, "of" second occurrence, should be -- to --.

Signed and Sealed this

Twenty-ninth Day of March 1977

[SEAL]

Attest:

RUTH C. MASON
*Attesting Officer*

C. MARSHALL DANN
*Commissioner of Patents and Trademarks*